United States Patent [19]
Chen et al.

[11] Patent Number: 4,904,245
[45] Date of Patent: Feb. 27, 1990

[54] SURGICAL VALVE ASSEMBLY FOR URINARY BLADDER IRRIGATION AND DRAINAGE

[75] Inventors: Allen Chen, Belleville, Mich.; Werner W. Ciupke, Sunnyvale, Calif.

[73] Assignee: Allen S. Chen, West Bloomfield, Mich.

[21] Appl. No.: 280,965

[22] Filed: Dec. 7, 1988

[51] Int. Cl.⁴ .............................................. A61M 1/00
[52] U.S. Cl. ...:.......................... 604/248; 137/625.47
[58] Field of Search ................... 604/247, 248, 27–30, 604/32; 137/625.41, 625.47; 251/207, 209

[56] References Cited

U.S. PATENT DOCUMENTS

| | | | |
|---|---|---|---|
| 3,306,171 | 2/1967 | Gordon | 137/625.47 |
| 3,626,938 | 12/1971 | Versaci | 137/625.47 |
| 3,780,736 | 12/1973 | Chen | 604/32 |
| 3,834,372 | 10/1974 | Turney | 604/248 |
| 3,927,693 | 12/1975 | Johnston | 137/625.47 |
| 4,784,637 | 11/1988 | Ryder | 604/248 |

Primary Examiner—Dalton L. Truluck
Assistant Examiner—Denise W. DeFranco
Attorney, Agent, or Firm—Barnes, Kisselle, Raisch, Choate, Whittemore & Hulbert

[57] ABSTRACT

An arrangement for irrigating a patient's bladder following prostate or bladder surgery which includes a valve body having five circumferentially spaced ports thereon and a valve core rotatable within the valve body and having passageways therein for interconnecting selective ports on the valve body when the core is rotated to predetermined positions for admitting irrigating fluid to the bladder through a urinary catheter and for conveniently draining the irrigating fluid from the bladder into a urinary drainage receptacle. The valve is constructed so that the entire irrigating and drainage procedure can be performed either intermittently or continuously without disconnecting the valve ports from the catheters or the irrigating supply and drainage receptacles employed in the arrangement.

12 Claims, 2 Drawing Sheets

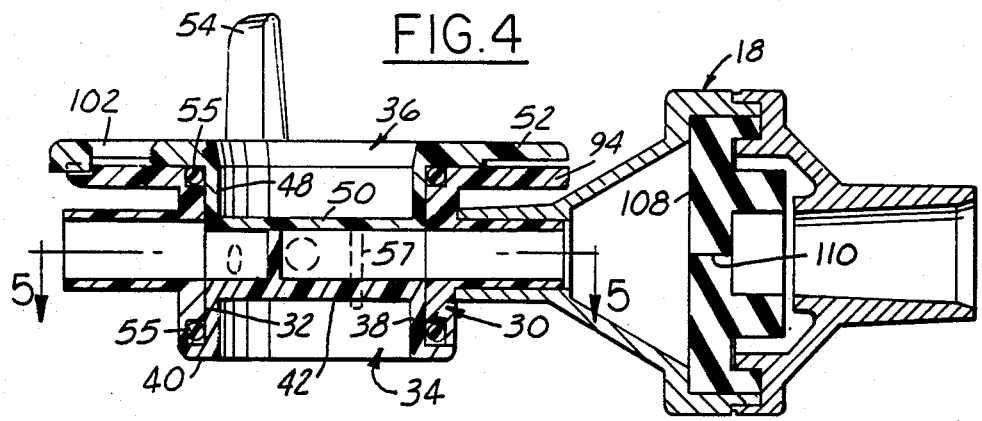
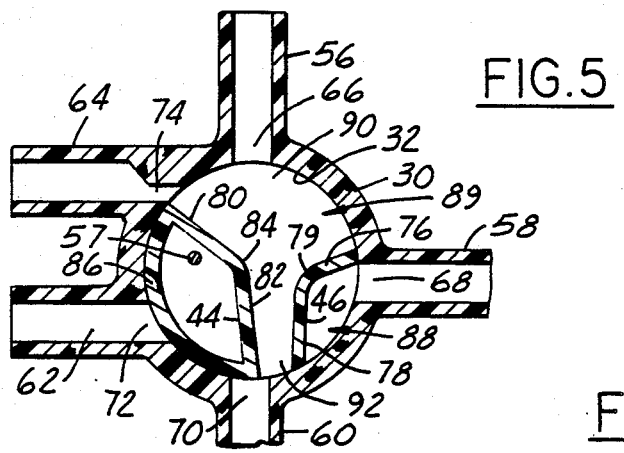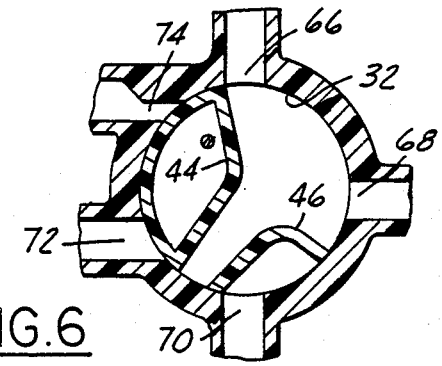
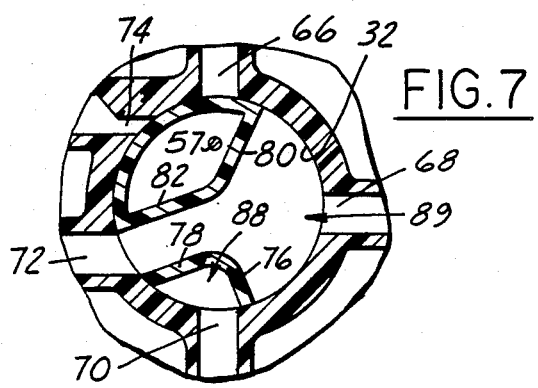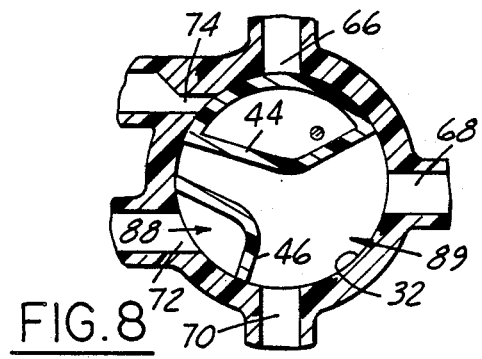
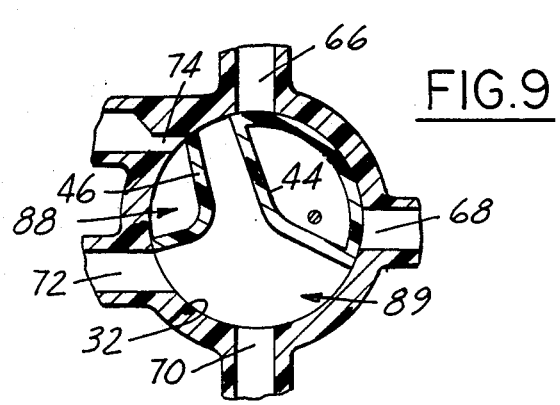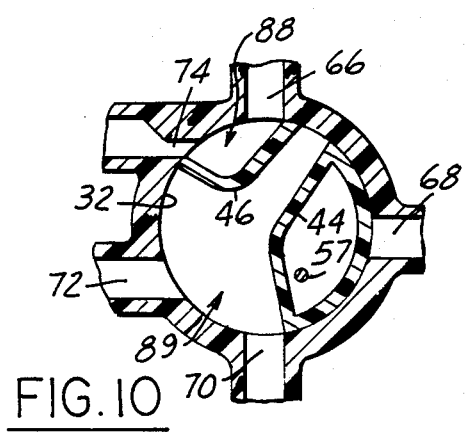

SURGICAL VALVE ASSEMBLY FOR URINARY BLADDER IRRIGATION AND DRAINAGE

The valve of the present invention is an improvement over the valve disclosed in the prior U.S. Pat. No. 3,780,736 to Chen. The valve disclosed in the prior Chen patent has four circumferentially spaced ports so arranged in relation to a rotatable valve core as to require the core to be rotated first in one direction and then in the opposite direction to specific positions between successive steps in the bladder irrigating procedure. Such reversal of rotation between successive irrigating steps can sometimes cause confusion in the mind of the nurse or other technician performing the procedure.

It is, therefore, one object of the present invention to provide a bladder irrigating valve of the type shown in said Chen patent which is so designed that the valve core is rotated incrementally in one direction to perform the required sequence of steps in the bladder irrigating procedure.

Following prostate or bladder surgery it is customary to irrigate the bladder periodically at regular intervals (for example, every fifteen or twenty minutes) until the drained irrigating fluid is clear and free of blood clots. However, in order to avoid or minimize painful bladder contractions resulting from the formation of blood clots, which in turn causes bleeding of the prostate or the surgical wound, it is sometimes desirable to irrigate the bladder continuously at a relatively slow selected rate between the successive intervals of customary irrigations. With the valve of the prior Chen patent and with irrigating procedures practiced without that valve, when this type of continuous irrigation is desired it becomes necessary to disconnect the urinary catheter from the valve or syringe for admitting fluid to the bladder and connect the catheter to another source of irrigating fluid and control the rate of flow, for example, 80 to 100 drops per minute, through another valve. This procedure has several inherent disadvantages. The connecting and disconnecting of catheters and other devices which may have blood thereon can lead to various infections to the administering personnel, especially in view of the increasing spread of A.I.D.S. In addition, this procedure is costly, not only from the standpoint of the apparatus employed, which is discarded after each single use, but also from the standpoint of the time necessarily consumed to connect and disconnect the bladder draining apparatus.

A further object of the present invention is to provide a valve that avoids these disadvantages in that it contains a fifth port in the valve body that enables the valve core to be rotated to a selected position to produce a slow regulated flow of irrigating fluid through the bladder and to the drainage receptacle.

In the drawings:

FIG. 4 is a sectional view along the line 4—4 in FIG. 2;

FIG. 5 is a sectional view along the line 5—5 in FIG. 4 and showing the valve core in the start or zero position;

FIGS. 6, 7, 8, 9 and 10 are views similar to FIG. 5 and showing the valve core in the first, second, third, fourth and fifth positions, respectively.

Figure 1:
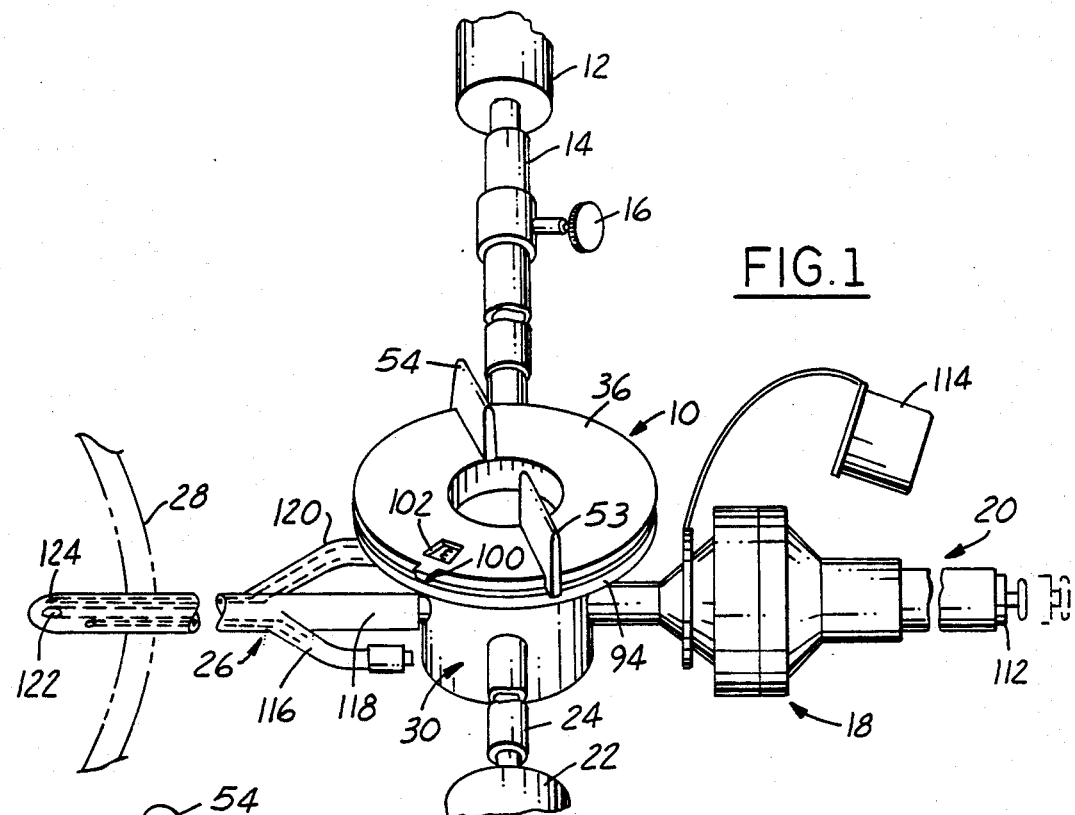
FIG. 1 is a somewhat diagrammatic perspective view of the valve of the present invention connected with a source of irrigating fluid, a urinary catheter, a syringe and a drainage receptacle in the manner contemplated for irrigating a patient's bladder.

In FIG. 1 the surgical valve generally designated 10 is shown connected to a supply receptacle 12 for irrigating fluid by means of a tubular conduit 14 having a fluid control valve 16 therein. Valve 10 has also connected therewith a split valve 18 having a syringe 20 attached thereto. A drainage receptacle 22 is connected to valve 10 by a tubular conduit 24. A urinary catheter 26 is also connected to valve 10 and is adapted to be inserted into the patient's bladder designated 28.

Figure 2:
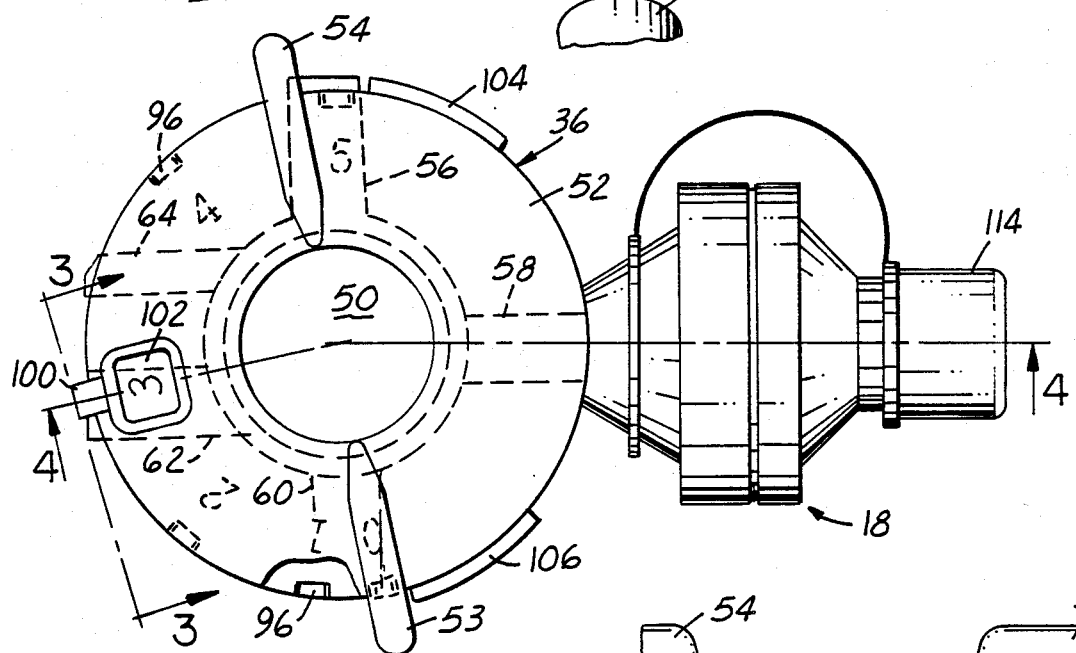
FIG. 2 is a top plan view of the valve showing a slit valve connected to the syringe port of the irrigating valve.
Figure 3:
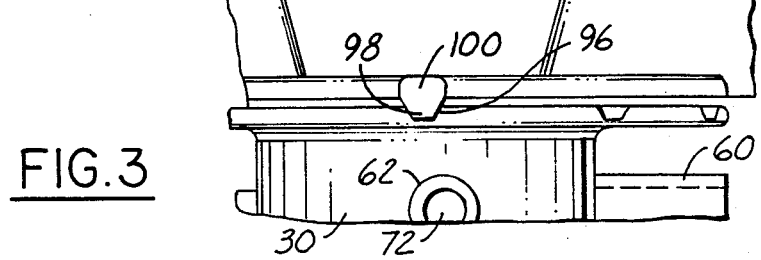
FIG. 3 is a fragmentary view along the line 3—3 in FIG. 2.

Referring now to FIGS. 2, 3 and 4, valve 10 comprises a molded plastic body 30 having a cylindrical through bore 32 in which a valve core 34 and a handle 36 are rotatably mounted. Valve core 34 has a cylindrical wall 38 having a close fit with bore 32 and terminates at its lower end in a radially outwardly extending flange 40. The upper end of cylindrical wall 38 is closed by a flat circular wall 42, on the top side of which are formed a pair of upstanding partition members 44,46 (FIG. 5).

Handle 36 is formed with a cylindrical wall 48 having a close fit with bore 32. The lower end of wall 48 is closed by a flat bottom wall 50. At the upper end of cylindrical wall 48 there is formed a radially outwardly extending flange 52 having a pair of upstanding diametrically opposite lugs 53,54 thereon. Core 34 and handle 36 are preferably molded from a plastic resin and are connected together in the manner illustrated in FIG. 4 by a fusion weld between the bottom face of wall 50 on the handle and the upper edges of partitions 44,46 on core 34. The close fit between cylindrical walls 38,48 and bore 32 forms a good seal between these parts which is enhanced by rubber O-rings 55. Before welding, core 34 and handle 36 are located rotatively relative to each other by a stud 57 on handle 36 projecting downwardly through a registering opening in wall 42 of core 34.

Body 30 of the valve is preferably a molded plastic part formed with five radial tubular extensions designated 56,58,60,62,64 . These extensions define a first port 66, a second port 68, a third port 70, a fourth port 72 and a fifth port 74 emanating radially from the central bore 32 in body 30 and located vertically between the walls 42 and 50 of the valve core 34 and handle 36. In the arrangement illustrated and considering the configuration of partitions 44,46, the second port 68 is spaced circumferentially from the first port 66 slightly more than 90 degrees and the third port 70 is located generally diametrically opposite the first port 66. The fourth port 72 and the fifth port 74 are located on the opposite side of body 30 from the second port 68 and are spaced apart circumferentially about 75–80 degrees.

Partition 46 comprises two angularly related segments 76,78 connected at their inner ends by a rounded shoulder 79. Partition 44 comprises two angularly related, upstanding segments 80,82 connected at their inner ends by a rounded shoulder 84 and interconnected at their outer ends by a circumferentially extending segment 86 having a close fit with the cylindrical bore 32 of body 30. The radially outer ends of segments 76,78 also have a close fit with the cylindrical bore 32 of body 30. The two connected segments 76,78 of partition 46 define a cavity or passageway 88 around a relatively short circular arc at the outer periphery of core 34. Likewise, the two partitions are spaced apart as shown to form a generally diametrically extending passageway 89 through core 34 having a relatively large end 90 and a relatively small end 92.

At its upper end body 30 has a radially outwardly extending circular flange 94 which underlies flange 52 on handle 36. The upper face of flange 94 has impressed thereon at accurately determined, circumferentially spaced locations the numerals 0, 1, 2, 3, 4 and 5. Radially outwardly of each of these numerals the periphery of flange 94 is formed with a shallow socket 96. When the assembly of core 34 and handle 36 is rotated it is adapted to be arrested at precisely located positions by means of a detent 98 adapted to engage with the successive sockets 96. Detent 98 is formed on the underside of a lug 100 at the outer periphery of flange 52 on handle 36. Radially inwardly of lug 100 flange 52 is formed with an window 102 through which the numerals on flange 94 are visible when the handle is rotated on body 30 by grasping lugs 54,56. The extent to which the handle 36 can be rotated in opposite directions is limited by a pair of lugs 104,106 at the outer periphery of flange 94. Lug 100 is adapted to abut against lug 104 to limit rotation of the handle in a clockwise direction to a position where the numeral 5 on flange 94 is visible through the opening 102 and lug 106 is abutted by lug 100 when the handle is rotated in a counterclockwise direction to a position wherein the numeral 0 is visible through the opening 102. The relative positions of the partitions 44,46 with respect to the ports on the body 30 in the positions 0, 1, 2, 3, 4, 5 are illustrated in FIGS. 5, 6, 7, 8, 9 and 10, respectively.

In use and as illustrated in FIG. 1, the tubular extension 56 which defines the first port 66 is connected to the irrigating fluid supply receptacle 12. The tubular extension 58 which defines port 68 has connected thereto the split valve 18 which, as shown in FIG. 4, is provided with a diaphragm 108 having a slit 110 cut therethrough which allows fluid to flow through the slit valve when the differential pressure across the diaphragm is on the order of three or four pounds per square inch. This pressure differential can be readily created by a reciprocation of the plunger 112 on syringe 20. The volume of syringe 20 is much greater than the volume of passageway 89. A removable cap 114 is provided for closing the open end of split valve 18 when the syringe 20 is removed therefrom. The tubular extension 60 on body 30 which defines the third port 70 is connected to the receptacle 22 which receives the fluid drained from the bladder. Catheter 26 is of a conventional type and comprises three lumens or passageways which at the proximate end of the catheter are connected with the forked extensions 116,118,120. The lumen of extension 116 connects with a balloon near the distal end of the catheter to inflate the same and prevent accidental retraction thereof. The extension 118 forms a rather large passageway in the catheter and is connected with the tubular extension 62 on body 30 which defines the fourth port 72. At the distal end of the catheter the passageway of extension 118 terminates in a large opening 122. The remaining extension 120 defines a small passageway in the catheter and is connected to the tubular extension 64 on the valve body 30 which defines the fifth port 74. At the distal end of the catheter the small passageway in extension 120 terminates in a small opening 124.

When it is desired to irrigate a patient's bladder the valve is connected to the various components as shown in FIG. 1 and the handle 36 is rotated to the position wherein the numeral 0 is visible through the opening 102. As pointed out previously, in this position the valve core 34 is rotated to the position shown in FIG. 5. The valve 16 controlling the flow of irrigating fluid from the container 12 is opened and fluid is permitted to flow through the large passageway 89 of core 34 and out through port 70 to the drainage container 22. Although a very small amount of the fluid may flow through port 74, the bulk of the fluid will be discharged through port 70 and air in the valve will be purged. After a very short interval of time handle 36 is rotated to position 1 wherein, as shown in FIG. 6, the large end passageway 89 in valve core 34 interconnects the first port 66 and the second port 68. The remaining third, fourth and fifth ports are sealed from each other in the bore 32 by the partitions 44,46. The plunger 112 is then retracted to draw a desired amount of irrigating fluid into syringe 20. Thereafter, handle 36 is rotated to position 2 wherein, as shown in FIG. 7, the second port 68 from the syringe communicates with the large end 90 of passageway 89 and the smaller end 92 of this passageway communicates with the fourth port 72 to which the extension 118 of catheter 26 is connected. Plunger 112 of syringe 20 is then pushed inwardly to direct the irrigating fluid through the valve and catheter into the patient's bladder. The plunger of the syringe is then retracted to withdraw the irrigating fluid containing the blood clots back into the syringe. Thereafter, handle 36 is rotated to position 3 shown in FIG. 8 and the plunger is advanced into the syringe to discharge the fluid to the drainage container 22 through the large end of passageway 89. Ports 66,72,74 are sealed with respect to each other and the bore 32 by the partitions 44,46. Handle 36 is then rotated counterclockwise back to position 1 and the steps described above at positions 1, 2 and 3 are repeated one or more times until the discharged irrigating fluid is substantially clear of blood clots.

Thereafter handle 36 is rotated to position 4 wherein the core 34 assumes the position illustrated in FIG. 9 wherein ports 70 and 72 communicate with each other through the large end of passageway 89. In this position the patient's bladder is permitted to drain in the normal urinary manner until such time as the next bladder irrigating procedure is initiated. However, in some instances, in order to avoid or minimize painful bladder contractions resulting from the forming of blood clots, which in turn causes bleeding of the prostate or the surgical wound, it is desirable to irrigate the bladder continuously at a relatively slow selected rate between the successive intervals of the customary bladder irrigations. Under such circumstances the handle 36 can be rotated to position 5 where the core 34 is oriented to the position shown in FIG. 10. In this position of the core, port 66 communicates with port 74 through the small peripheral passageway 88 and port 72 communicates with the drainage port 70 through the large end of passageway 89. Valve 16 is adjusted to obtain the desired relatively slow rate of flow of the irrigating fluid which is directed to the bladder through the extension 120 of the catheter and discharged therefrom through the extension 118, port 74, large passageway 90 and the discharge port 70.

It will be appreciated that with the valve core 34 in position 5 (FIG. 10), if desired, the inlet tubular extension 56 can be connected with a source of fluid other than irrigating fluid, such as in a chemotherapy treatment, to introduce desired medications into the patient's bladder. Also, with the valve core in position 5, if valve 16 in supply line 14 is closed, the bladder can drain in the normal urinary manner through port 72 as previously described. Therefore, it will be apparent that position 4 can be eliminated if desired and the valve construction modified accordingly.

After each irrigating procedure is completed the syringe 20 can be disconnected from the split valve 18 and the inlet of the split valve can be closed with the cover 114. The valve can then remain connected to the other components as illustrated in FIG. 1 until the next irrigating procedure is initiated, at which time a clean syringe can be connected to the split valve 18.

It will be observed that in performing the successive steps of a complete irrigation procedure, handle 36 is rotated incrementally in a clockwise direction from the 0 position to the numeral 5 position and is prevented from being rotated beyond these two extreme positions by the abutment of lug 100 with the ends of lugs 104,106. It will also be noted that the upstanding lugs 53,54 which are adapted to be gripped between the operator's fingers to rotate the handle are perpendicularly related in position to the window 102. Thus, the user's hand or fingers will not obstruct the view through window 102 and the inadvertent mislocation of the rotative position of the valve core is avoided.

We claim:

1. In a catheter arrangement for irrigating a patient's bladder the combination comprising a valve body having a circular bore and a circular cylindrical core rotatively retained in said bore, said body having first, second, third, fourth and fifth ports spaced successively around the periphery of the body and communicating with said bore, said first port being connected with a source of irrigating fluid, the second port being connected to a syringe, the third port being connected to a drainage fluid container, the fourth port being connected to a first lumen of a urinary catheter adapted to be extended into the patient's bladder and the fifth port being connected to a second lumen of said catheter, said core having first and second separate and distinct passageways therein, said first passageway having generally diametrically opposite ends extending to said bore, one of said ends having a dimension circumferentially of said bore much larger than the other end, said second passageway being located at one side of said first passageway, said passageways and ports being dimensioned and arranged circumferentially relative to each other so that in a first rotative position of said core the large end of said first passageway communicates with both the first and second ports, the small end of the first passageway is sealed by said bore and the remaining ports are sealed from said first passageway and from each other by said core so that the syringe can be operated to draw a quantity of irrigating fluid from said source through said large end of said first passageway and into the syringe, said core being rotatable in one direction from said first position to a second position wherein said large end of said first passageway connects with said second port, the smaller end of the first passageway connects with said fourth port and the first, third and fifth ports are sealed from each other and from said first passageway by said core so that the syringe can be operated first to discharge the fluid therein through said first passageway and into the first lumen of the catheter and then to draw the fluid from the bladder back into the syringe through said first lumen, said core being rotatable in said one direction from said second position to a third position wherein said large end of the first passageway communicates with both the second and third ports, the small end of the first passageway is sealed by said bore and the remaining ports are sealed from each other and from said first passageway by said core so that the syringe can be operated to discharge the fluid therein that has been withdrawn from the bladder into said drainage container through said large end of the first passageway, said core being rotatable still further in said one direction from said third position to a last position wherein the large end of the first passageway communicates with both the third and fourth ports and the second passageway interconnects the first and fifth ports and the second port is sealed from said passageways and from the remaining ports by said core to permit irrigating fluid to be directed into the bladder at a controlled rate through the second passageway and the second lumen of the catheter and simultaneously drained from the bladder through the first lumen or, in the alternative, when flow of fluid from the source is arrested, to permit the patient's bladder to drain in an ordinary urinary manner through said first lumen into said drainage container.

2. The combination called for in claim 1 wherein the core is rotatable to a fourth position located intermediate said third and last positions wherein said large end of said first passageway communicates with said third and fourth ports, the smaller end of the first passageway is sealed by said bore and the remaining ports are sealed from said first passageway and from each other by said core.

3. The combination called for in claim 1 wherein the core is rotatable to a start position advanced from said first position wherein said main passageway interconnects the first and third ports so that irrigating fluid can be directed from the supply container directly to the discharge container in order to purge air from said main passageway.

4. The combination set forth in claim 1 wherein the second passageway is formed around a portion of the outer periphery of said core.

5. The combination set forth in claim 1 wherein said core is a generally hollow member and said passageways are defined by two spaced partitions in said core, each of said partitions having a pair of radially extending angularly related segments, the radially inner ends of the segments of each partition being connected in sealed relation and the radially outer ends of the segments being in close fitting sealed relation with said bore.

6. The combination set forth in claim 5 wherein the outer ends of one of said partitions are interconnected so that the second passageway is defined by the space on the radially outer side of said one partition.

7. The combination called for in claim 6 wherein the outer ends of the other partition are interconnected by an arcuate flange which seals the space on the radially outer side of said other partition from said bore.

8. The combination set forth in claim 1 wherein the larger end of said first passageway is of sufficient circumferential extent to span the fourth and fifth ports, and means are provided for preventing rotation of the core in said one direction beyond said last position sufficiently to enable the larger end of the said main passageway to interconnect the fourth and fifth ports.

9. The combination set forth in claim 1 including interengagable detent means on the core and valve body adapted to resiliently interengage in each of said positions so as to indicate to the user that the core is rotated to a selected one of said positions.

10. The combination set forth in claim 1 wherein said valve body has a radially outwardly extending flange at one end thereof, said flange having a series of indicia indicated thereon, each of said indicia being located in accurately predetermined, circumferentially spaced relation with respect to a corresponding one of said ports, said core having a radially extending annular flange thereon overlying the annular flange on the body and concealing the indicia thereon and window means at a predetermined single position on the core flange enabling visual observation of the underlying one of said indicia on the body flange when the core is rotated to any one of said positions.

11. The combination set forth in claim 10 including a pair of diametrically opposed, upstanding lugs on said core flange for facilitating manual rotation of said core, said lugs being generally perpendicularly related to said window means.

12. The combination set forth in claim 1 including means on the body and core adapted to abut and thereby prevent rotation of the core in the opposite direction from said first position to a position wherein the large end of the first passageway spans and interconnects the fourth and fifth ports.

* * * * *